United States Patent [19]

McSpadden

[11] Patent Number: 5,083,923

[45] Date of Patent: Jan. 28, 1992

[54] METHOD OF OBTURATING AN EXTIRPATED ROOT CANAL

[76] Inventor: John T. McSpadden, 6918 Shallowford Rd., Chattanooga, Tenn. 37421

[21] Appl. No.: 532,588

[22] Filed: Jun. 4, 1990

[51] Int. Cl.$^5$ .............................................. A61C 5/02
[52] U.S. Cl. ...................................... 433/224; 433/81
[58] Field of Search .................................. 433/81, 224

[56] References Cited

U.S. PATENT DOCUMENTS

| 4,353,698 | 10/1982 | McSpadden | 433/164 |
| 4,457,710 | 7/1984 | McSpadden | 433/81 |
| 4,681,545 | 7/1987 | Lapcevic | 433/224 |
| 4,931,096 | 6/1990 | Fujisawa et al. | 433/224 |

OTHER PUBLICATIONS

Grassi, Michael D., et al; Changes in the Physical Properties of the Ultrafil Low-Temperature (70° C.) Thermoplasticized Gutta-percha System; *Journal of Endodontics*; vol. 15, No. 11, Nov. 1989; pp. 517-521.

*Primary Examiner*—Gene Mancene
*Assistant Examiner*—Adriene B. Lepiane

*Attorney, Agent, or Firm*—Luedeka, Hodges, Neely & Graham

[57] ABSTRACT

A method of obturating an extirpated root canal utilizes two types of filler material, one type of which is in the form of a gutta-percha point and the other type of which is a thermoplasticized gutta-percha having a melting temperature of about 15° to 20° C. less than the melting temperature of the gutta-percha point. The steps of the method include the introducing of an initial amount of thermoplasticized gutta-percha in a heated and softened condition into the root canal so that the initial amount fills the bottom of the canal. A gutta-percha point is then positioned within the root canal and another amount of thermoplasticized gutta-percha is introduced in a heated and softened condition into the canal. The thermoplasticized gutta-percha is then manipulated into contact with the portion of the gutta-percha point positioned within the root canal so that the gutta-percha point is fed into and compacted within the root canal with the thermoplasticized gutta-percha. Additional amounts of thermoplasticized gutta-percha are introduced and manipulated into contact with additional gutta-percha points as necessary to fill the root canal with a core of filler material.

7 Claims, 3 Drawing Sheets

METHOD OF OBTURATING AN EXTIRPATED ROOT CANAL

BACKGROUND AND SUMMARY OF THE INVENTION

The present invention relates generally to the field of endodontics and relates more particularly to processes for filling stripped root canals.

Known methods of obturating (filling) an extirpated (stripped) root canal commonly involve the insertion of strand-like pieces of gutta-percha known as points into the root canal and the use of compacting tools known as plungers and spreaders to compact the gutta-percha points within the canal. Typically, the compacting tools are heated to soften the gutta-percha points in the canal and then hand manipulated to progressively feed and compact the points in the canal. Additional points are fed to the canal as the compacting operation progresses in order to fill the canal with gutta-percha.

Another known method of obturating an extirpated root canal involves the insertion of gutta-percha points into the root canal and manipulating the shank of a high-speed, rotating instrument into contact with the gutta-percha points so that frictional heat generated at the instrument shank softens the gutta-percha. With the gutta-percha in a softened condition, it is compacted within the canal with manipulations which include reciprocating motions of the instrument shank.

Limitations associated with known obturation methods relate to the general difficulty in filling of the root canal with filler material so that any voids or fissures associated with the canal wall are filled and the utilization of relatively large and/or high-speed rotating instruments to compact the material within the canal. Unless an endodontist who performs known obturating techniques is highly skilled, all voids and fissures of the canal are not always filled satisfactorily. In addition, reciprocating motions of a relatively large compacting instrument against filler material positioned within a canal increase the possibility that the apical foramen will be extruded by the filler material. Moreover, utilization of any high-speed rotating instrument within a mouth requires a great deal of care to prevent injury to the patient or keep from fracturing the instrument.

It would be desirable to provide a new method for obturating an extirpated root canal with a greater likelihood that gutta-percha compacted within the root canal conforms to the shape of the wall of the root canal and that fissures or similar openings associated with the canal wall are completely filled with gutta-percha.

Another object of the present invention is to provide such a method which obviates the use of large and/or high-speed rotating instruments for compacting filler material within a root canal.

More particularly, the present invention is directed to the obturating of an extirpated root canal with two types of filler material wherein one type of filler material is provided in the form of a gutta-percha point having a predetermined melting temperature and wherein the other type of filler material is provided in the form of a thermoplasticized gutta-percha having a melting temperature of about 15° to 20° C. less than that of the melting temperature of the gutta-percha point. Steps in the method include the introduction of an initial amount of thermoplasticized gutta-percha in a heated, softened condition into the root canal so that the initial amount fills the bottom of the canal. At least a portion of the gutta-percha point is then positioned into the root canal, and another amount of thermoplasticized gutta-percha in a heated, softened condition is introduced into the canal. The another amount of thermoplasticized gutta-percha is then manipulated into contact with the portion of the gutta-percha point positioned within the canal so that the gutta-percha point is fed into and compacted within the root canal with the amounts of thermoplasticized gutta-percha.

Because the thermoplasticized gutta-percha introduced into the canal is a fluid in its heated and softened condition, the apical foramen and any fissures or voids associated with the canal wall are suitably coated and/or filled by the thermoplasticized gutta-percha with no need that filler material be forcibly urged, such as by reciprocating motions of a compacting instrument, into the canal. Thus, the endodontist performing the method of this invention need not possess as high a degree of skill as in prior methods in order to satisfactorily fill the root canal, and the possibility that the apical foramen will be extruded by filler material is reduced by this method. In addition, the heat necessary for softening and rendering workable the gutta-percha point material is absorbed by the point material from the heat of the softened thermoplasticized material. Thus, the method of the invention obviates any need for the manipulation of a high-speed rotating instrument within the canal for the purpose of generating frictional heat.

A more complete understanding of the present invention will be had by reference to the specification and accompanying drawings wherein like numerals refer to like parts throughout.

DETAILED DESCRIPTION OF THE ILLUSTRATED EMBODIMENT

Figure 1:
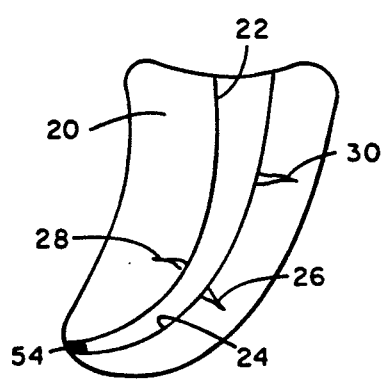
FIG. 1 is a cross-sectional view of a tooth having an extirpated root canal prepared for filling in accordance with the method of this invention.

There is illustrated in FIG. 1 a tooth 20 having a root canal 22 which has been extirpated (stripped) in preparation of an obturating (filling) process in accordance with an embodiment of the method of the invention. The root canal 22 has been extirpated in accordance with well known procedures which remove dead or damaged tissue from the canal 22 in order to provide a space 24 for accepting filler material inserted and compacted therein. In the depicted tooth 20, there are illustrated fissures 26, 28, 30 defined within the wall of the root canal 22 which are ordinarily difficult to fill by conventional obturating processes. As will be apparent herein, by feeding and compacting two types of filler material within the root canal 22 in accordance with the steps of this invention, the entire space 24 of the root canal 22 and the fissures 26, 28, 30 defined along the root canal wall are completely filled with filler material.

Figure 2:
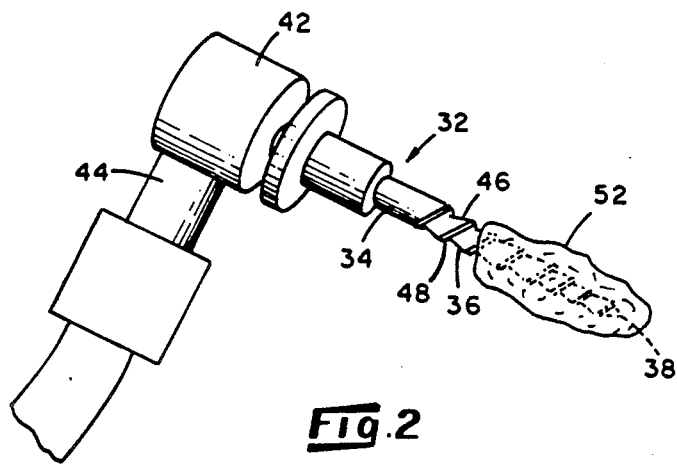
FIG. 2 is a fragmentary elevational view of a compacting instrument having a rotatable shank which has been coated with a softened gutta-percha filler material.

With reference to FIG. 2, there is shown an exemplary instrument 32 of a type used to spread and compact filler material within the root canal space 24. The instrument 32 includes a rotatable shank 34 having a working portion 36 extending along a substantial portion of the shank length and terminating at a pilot tip 38. When performing the obturating method described herein, the instrument 32 is rotated within a root canal at relatively slow speeds. To this end, the portion of the shank 34 above the working portion 36 is provided with a fitting which is adapted to mate with the chuck 42 of a dental handpiece 44 for powering the rotation of the instrument 32 at low speeds or to mate with a handle (not shown) facilitating rotation and manipulation of the instrument 32 by hand.

Although the working portion 36 of the instrument shank 34 may take any of a number of forms, the depicted working portion 36 includes at least one helical flute 46 extending along the length of the working portion 36 so as to provide a downwardly-directed shoulder 48 which spirals along the length of the working portion toward the tip 38 thereof. When the shank 34 is rotated within a root canal in an appropriate direction, filler material which comes into contact with the shank 34 is urged by the shoulder 48 downwardly toward and off of the tip 38.

Figure 5:
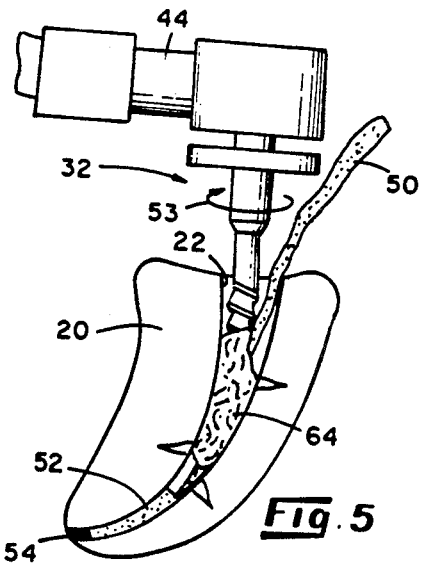
Figure 6:
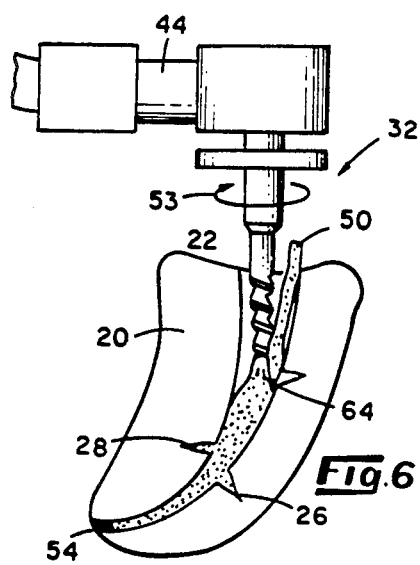

In accordance with the method described herein, two types of filler material are used to obturate the canal 22. One type of filler material, indicated 50 in FIG. 5, is provided in the form of a strand-like piece of gutta-percha, commonly known as a point. Normally, gutta-percha points are solid in form at room temperature, e.g., about 24° C., so that heat must be applied to the points in order to render the points soft and pliable for compaction within a root canal. Although gutta-percha points may possess a melting temperature within a relatively broad range, it has been found that gutta-percha material possessing a melting temperature of no less than about 50° C. is well-suited for use in the obturating process described herein.

Heat is transferred to the gutta-percha point 50 in a manner described herein to render the point soft and workable within the root canal 22. Once softened to a workable condition, the gutta-percha of the point 50 may be compacted within the root canal 22 by the instrument 32. As the lower portion of the gutta-percha is compacted by the instrument 32, the upper end of the point 50 is drawn downwardly into the canal 22 so that the material of the point 50 is continually fed to the site at which the material is compacted.

The second type of filler material, indicated 52 in FIG. 2, is a thermoplasticized gutta-percha having a melting temperature which is about 15° to 20° C. lower than that of the gutta-percha point material described above. An exemplary filler material found to be well-suited as the thermoplasticized gutta-percha for the process described herein is available under the trade designation Ultrafil from Hygenic Corp. of Akron, Ohio. Physical properties, including the melting temperatures, of Ultrafil material are discussed in an article entitled "Changes in the Physical Properties of the Ultrafil Low-Temperature (70° C.) Thermoplasticized Gutta-percha System" appearing on pages 517-521 in the November, 1989 issue of the *Journal of Endodontics* and which is incorporated herein by reference.

As will be apparent herein, the thermoplasticized gutta-percha amount 52 is worked with the rotating shank 34 of the compacting instrument 32 in order to compact the amount 52 within the canal. However, Ultrafil and like materials are relatively firm at room temperature. Consequently, such filler material must be heated in order to render the material soft and pliable. Such heating may be effected external to the root canal by placing the material within a suitable container and by either rotating an instrument within the container (to generate frictional heat) or by applying heat to the outside of the container.

For introduction of thermoplasticized gutta-percha 52 into a root canal, the thermoplasticized gutta-percha, after being heated to a softened condition, is applied to the shank 34 of the compacting instrument so as to coat the shank 34 as depicted in FIG. 2, and then introduced into the canal by inserting the coated shank 34 into the canal. The instrument shank 32 may be appropriately coated with thermoplasticized gutta-percha by simply dipping the shank 32 into a quantity of the softened material which, in turn, adheres to the shank 32.

Figure 3:
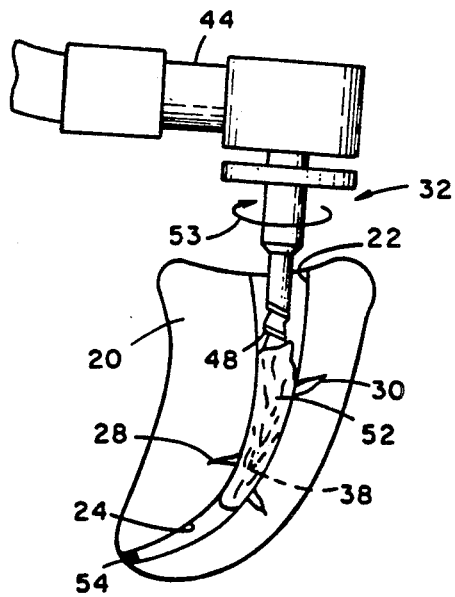
FIGS. 3-10 are views similar to that of FIG. 1 illustrating in sequence the various steps in obturating the root canal of the tooth of FIG. 1.
Figure 4:
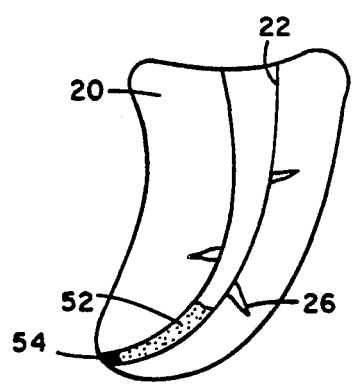

To perform the obturating process, the coated shank 34 of the instrument 32 is inserted into the root canal 22 as illustrated in FIG. 3 so that the shank tip 38 is positioned adjacent the apical foramen 54. The shank 34 is then rotated about its longitudinal axis in the direction of the arrow 53 to urge the amount 52 of thermoplasticized gutta-percha downwardly and off of the shank tip 38. Once the amount 52 has been urged off of the shank 34 so that the bottom of the canal 22 is filled with the amount 52 as illustrated in FIG. 4, the shank 34 is removed from the canal 22.

An advantage provided by the aforedescribed step of introducing an amount 52 of thermoplasticized gutta-percha into the canal 22 relates to the conformance of the amount 52 to the apical portion of the canal. In its heated and softened condition, the thermoplasticized gutta-percha amount 52 possesses a relatively low viscosity so that when introduced into the bottom of the canal 22, the amount 52 easily flows along the surface of the apical foramen 54 so as to completely cover the apical portion of the canal 22. Thus, there is no need to urge filler material downwardly into the canal 22 with reciprocating or "chopping" motions of a compacting tool which may otherwise be required with a less "fluid" filler material and which increases the likelihood of extrusion of the apical foramen with the filler material.

Next, the gutta-percha point 50 is positioned within the root canal 22 as illustrated in FIG. 5 so that the lower end of the point 50 is positioned adjacent the bottom of the canal 22. An additional amount, indicated as 64, of thermoplasticized gutta-percha is then applied to the shank 34 of the compacting instrument 32 in a heated and softened condition, and the coated shank 34 is inserted into the root canal 22 as illustrated in FIG. 5 so that the shank tip 38 is positioned adjacent the apical foramen 54.

The instrument 32 is then energized to rotate the shank 34 and appropriately manipulated with the hand so that the amount of thermoplasticized gutta-percha 64 which coats the shank 34 contacts the lower portion of the point 50. As the shank 34 continues to be rotated and the filler materials amounts 50 and 64 contact one another, heat from the thermoplasticized gutta-percha amount 64 is absorbed by the gutta-percha of the point 50 so that the point 50, and in particular the lower portion of the point 50, becomes softened and mixes with the thermoplasticized gutta-percha 52. Satisfactory mixing of the thermoplasticized gutta-percha with the point material may be effected by rotating the instrument shank 34 as slowly as 25 rpm.

Figure 7:
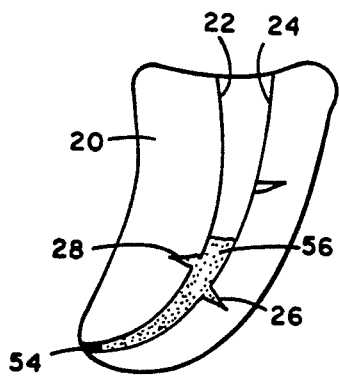

As the mixing of the material amounts 50 and 64 continues, the shank 34 is continually manipulated to work the softened material mix into a desired region of the canal space 24, and the upper portion of the point 50 is drawn downwardly into the canal 22 where it is compacted with the thermoplasticized gutta-percha. Hand manipulations of the instrument 32 which move the shank 34 along its longitudinal axis in a reciprocating manner may be helpful in directing the softened material mix into a desired region of the canal space 24. Upon complete mixing or displacing of the point 50 with the amount of thermoplasticized gutta-percha 64 as illustrated in FIG. 7 so that the filler material mix, indicated as 56, is positioned adjacent the bottom of the canal 22, the instrument shank 34 is removed from the canal 22.

Figure 8:
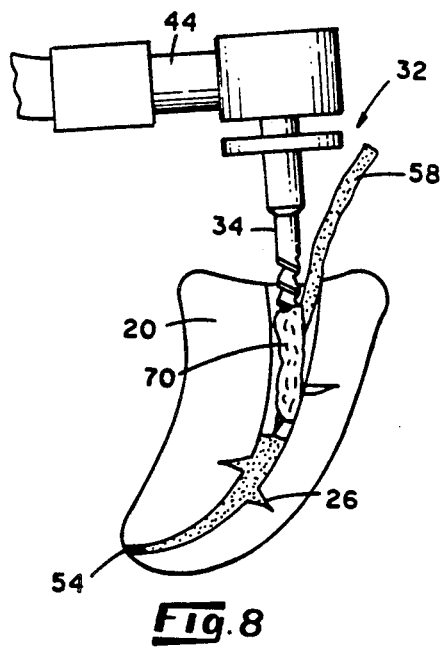
Figure 9:
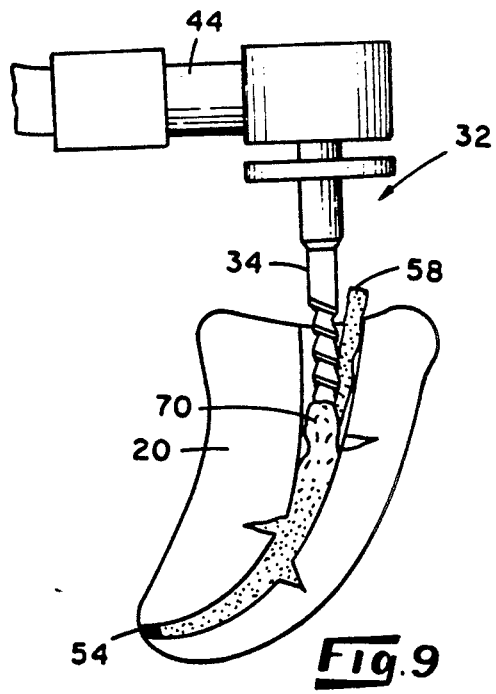
Figure 10:
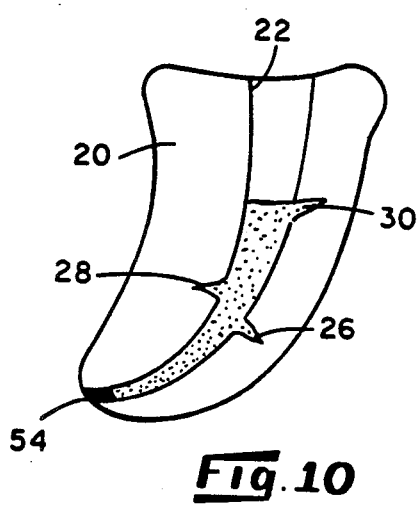

With the instrument shank 34 removed from the canal 22, an additional gutta-percha point 56 (FIG. 8) is placed within the canal 22 so that the lower portion of the point 56 is positioned adjacent the filler material mix 56 previously compacted within the canal 22. An additional amount 70 (FIG. 8) of heated thermoplasticized gutta-percha is then applied to the shank 34 of the instrument 32, and the shank 34 is then inserted and rotated within the canal 22. By appropriate manipulation of the rotating shank 34 so that the amount 70 of thermoplasticized gutta-percha engages the point 58, the lower portion of the second point 58 becomes softened and mixes with the amount 70 of thermoplasticized gutta-percha. As the point 58 continues to be mixed with the amount 70, the upper portion of the point 58 is drawn downwardly into the canal 22, as illustrated in FIG. 9. Meanwhile, the shank 34 continues to be manipulated to compact the mixed material of the point 58 and amount 70 atop the filler material mix 56. Upon completion of the compacting and mixing of the point 58 and the amount 70 within the canal 22 as illustrated in FIG. 10, the instrument shank 34 is removed from the canal 22.

Figure 11:
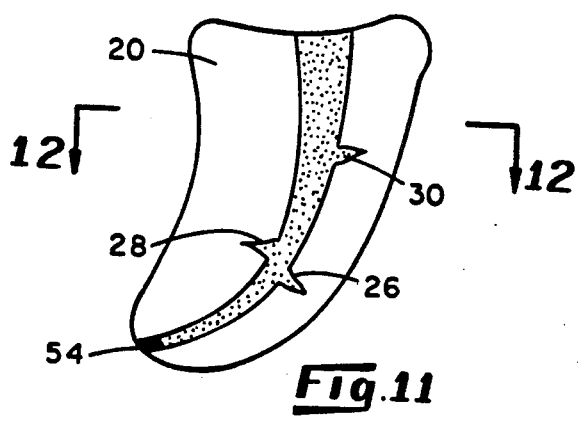
FIG. 11 is view similar to that of FIG. 1 illustrating the canal when completely filled with filler material.

The steps of inserting a gutta-percha point within the canal 22, applying an amount of heated thermoplasticized gutta-percha to the instrument shank 34, inserting and rotating the shank 34 within the canal 22 to mix and compact the gutta-percha point with the thermoplasticized gutta-percha within the root canal 22 are thereafter repeated as necessary until the root canal space 24 is completely filled with filler material as illustrated in FIG. 11. The filled root canal may thereafter be finished by conventional techniques.

Figure 12:
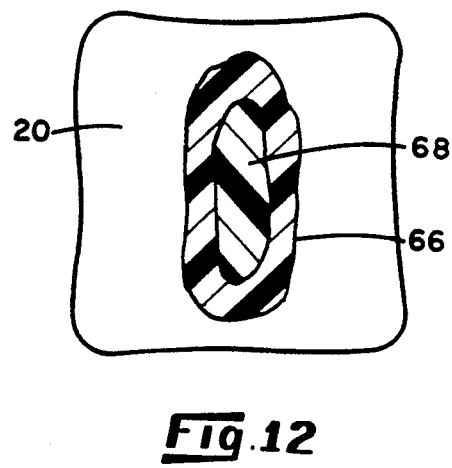
FIG. 12 is a schematic cross-sectional view taken about on line 12—12 of FIG. 11.

Another advantage provided by the aforedescribed obturating process relates to the filling of the fissures 26, 28, 30 and similar openings defined in the wall of the extirpated root canal 22. More specifically, as the filler materials are mixed and worked against the wall of the root canal 22, the filler material of the mix flows within so as to completely fill the canal wall fissures 26, 28, 30. It is believed that such a complete filling of the fissures 26, 28, 30 is effected as the thermoplasticized gutta-percha, which is more "fluid" in its heated and softened condition than is the softened material of the gutta-percha points, forms a perimetal layer 66 (FIG. 12), comprised primarily of thermoplasticized gutta-percha, about a core 68, comprised primarily of gutta-percha point material. Consequently, as the perimetal layer 66 of the mixed filler material amounts is moved along the root canal wall, the "fluid" thermoplasticized gutta-percha readily conforms to the shape of the canal wall and flows into the fissures 26, 28, 30 opening out of the wall. The core 68 of the filler material mix subsequently cures to a solid, relatively rigid condition within the canal and ensures that the filler material mix which cures within the canal 22 is firmly held therein.

Still another advantage of the aforedescribed process relates to the fact that because the heat needed to soften and render workable the gutta-percha point material is absorbed by the point material from the thermoplasticized gutta-percha amounts, there is no need to generate frictional heat or provide extraneous heat within the root canal 22 that may threaten injury to the tissues supporting the tooth. Consequently, an endodontist may use a smaller and slower-rotating compacting instrument when compacting the mix than what otherwise may be required to generate frictional heat within the canal 22. Instead and as mentioned earlier, the endodontist may use a manual instrument to work and compact the filler materials together. In addition, any need for a larger instrument to "chop" point material into a softened condition and heating by the friction generated by the instrument within the canal is obviated, and any likelihood of injury to the apical foramen 54 or some other region of the root canal 22 from instrument-applied pressure is thereby reduced.

The foregoing detailed description is given primarily for understanding of the invention and no unnecessary limitations are to be understood therefrom for modifications will become obvious to those skilled in the art upon reading this disclosure and may be made without departing from the spirit of the invention and the scope of the appended claims.

I claim:

1. A method of obturating an extirpated root canal with two types of filler material wherein one type of filler material is provided in the form of a gutta-percha point having a predetermined melting temperature and wherein the other type of filler material is provided in the form of a thermoplasticized gutta-percha having a melting temperature within the range of about 15 to 20 Celsius degrees less than that of the melting temperature of the gutta-percha point, said method comprising the steps of:

positioning at least a portion of a gutta-percha point within the root canal;

providing a compacting instrument having a tipped shank which when rotated within the root canal in one direction and moved into contact with filler material urges the filler material toward and off of the tip of the shank;

coating the shank of the compacting instrument with an amount of thermoplasticized gutta-percha in a heated, softened condition;

introducing the coated shank of the compacting instrument into the root canal; and rotating the shank in the one direction and manipulating the amount of thermoplasticized gutta-percha coated about the shank into contact with the portion of the gutta-percha point positioned within the root canal so that the gutta-percha point is fed into and compacted within the root canal with the amount of thermoplasticized gutta-percha as the thermoplasticized gutta-percha and the gutta-percha point are urged toward and off of the tip of the shank.

2. The method as defined in claim 1 wherein the steps of introducing at least a portion of a gutta-percha point within the root canal, coating the shank of the compacting instrument, introducing the coated shank into the root canal and rotating the shank and manipulating the amount of thermoplasticized gutta-percha coated about the shank into contact with the gutta-percha point are repeated as necessary with additional points and amounts of thermoplasticized gutta-percha to fill the root canal with a core of filler materials.

3. The method as defined in claim 1 wherein the step of rotating the shank of the instrument effects a mixing of the thermoplasticized gutta-percha with the material of the gutta-percha point.

4. The method as defined in claim 1 wherein the step of rotating and manipulating further includes the step of moving the shank of the compacting instrument in a reciprocating fashion within the root canal.

5. The method as defined in claim 1 wherein the step of coating the shank with an amount of thermoplasticized gutta-percha is preceded by the steps of:
providing an amount of thermoplasticized gutta-percha in an unheated, relatively firm condition and
heating so as to soften said amount for application to the shank of the compacting instrument.

6. The method as defined in claim 1 wherein the step of rotating and manipulating includes the step of working the thermoplasticized gutta-percha about the material of the gutta-percha point so that heat is transferred from the thermoplasticized gutta-percha to the gutta-percha point so as to soften the gutta-percha point.

7. The method as defined in claim 1 wherein the step of positioning at least a portion of a gutta-percha point within the root canal is preceded by the step of introducing an initial amount of thermoplasticized gutta-percha in a heated, softened condition into the root canal so that the initial amount fills the bottom of the canal.

* * * * *